US006821283B2

(12) United States Patent
Barzell et al.

(10) Patent No.: US 6,821,283 B2
(45) Date of Patent: Nov. 23, 2004

(54) SUTURING SYSTEM AND METHOD (75) Inventors: Winston E. Barzell, Sarasota, FL (US); Willet F. Whitmore, Sarasota, FL (US); Stephen E. Brauner, Bradenton, FL (US); Roger Wilson, Sarasota, FL (US)

(73) Assignee: CIVCO Medical Instruments, Inc., South Kalona, IA (US)

( * ) Notice: Subject to any disclaimer, the term of this patent is extended or adjusted under 35 U.S.C. 154(b) by 0 days.

(21) Appl. No.: 10/272,333

(22) Filed: Oct. 16, 2002

(65) Prior Publication Data

US 2004/0078046 A1 Apr. 22, 2004

(51) Int. Cl.[7] .............................................. A61B 17/04
(52) U.S. Cl. ...................................... 606/144; 606/148
(58) Field of Search ................................. 606/144, 148

(56) References Cited

U.S. PATENT DOCUMENTS

| | | | |
|---|---|---|---|
| 4,553,543 A | 11/1985 | Amarasinghe | |
| 5,591,179 A | 1/1997 | Edelstein | |
| 5,653,717 A | 8/1997 | Ko et al. | |
| 5,662,663 A | 9/1997 | Shallman | |
| 5,697,941 A | 12/1997 | Christy | |
| 5,741,276 A | 4/1998 | Polokyo et al. | |
| 5,810,849 A | 9/1998 | Kontos | |
| 6,080,167 A | 6/2000 | Lyell | |
| 6,143,004 A | 11/2000 | Davis et al. | |
| 6,206,893 B1 | 3/2001 | Klein et al. | |
| 6,238,404 B1 | * 5/2001 | Hidalgo et al. | ............. 606/148 |
| 6,358,258 B1 | 3/2002 | Arcia et al. | |
| 2001/0049537 A1 | 12/2001 | Kortenbach | |

FOREIGN PATENT DOCUMENTS

WO    WO 97/47246 A1    12/1997

* cited by examiner

*Primary Examiner*—Gary Jackson
(74) *Attorney, Agent, or Firm*—Fleit Kain Gibbons Gutman Bongini & Bianco; Paul D. Bianco; Martin Fleit (57) ABSTRACT

A suturing system and method for suturing first and second tissue sections is described. The system includes an elongate member having paired distal and proximal channels. The distal channel extends in the elongate member from the proximal end to a distal aperture and receives the distal end portion and at least a part of the body portion of a suture. The first proximal channel extends in the elongate member from the proximal end to a first proximal aperture and receives the proximal end portion and at least a part of the body portion of the suture. The elongate member is positioned between the first and second tissue sections with the suture in the first distal and first proximal channels such that a part of the body portion extends from the proximal end of the elongate member. The distal end of the suture passes through the first tissue section and the proximal end of the first suture passes through the second tissue section. The elongate member can be provided with other paired channels for additional sutures.

20 Claims, 11 Drawing Sheets

SUTURING SYSTEM AND METHOD

FIELD OF THE INVENTION

The present invention relates generally to a system and method for suturing first and second tissue sections, and more specifically to an anastomosis system and method particularly useful in minimally invasive procedures.

BACKGROUND OF THE INVENTION

The vast majority of surgical procedures require suturing of first and second tissue sections. This suturing can be time consuming. Additionally, if a laparoscopic or otherwise minimally invasive approach is used, accurate suture placement can be both time consuming and difficult to achieve.

Despite these concerns, minimally invasive surgical and interventional procedures have become widespread. Many of these procedures require anastomosis, i.e. connection of hollow structures. For example, radical prostatectomy, the complete surgical removal of the prostate gland as a treatment for prostate cancer, entails the removal of the prostate gland along with its fascial coverings and requires amputating the junctions of the prostate to the urethra at the urogenital diaphragm and to the urinary bladder at the bladder neck. To restore continuity of the urinary tract where the prostate has been removed, a new connection (anastomosis) of the bladder neck to the urethra must be accomplished.

This is the most challenging part of the radical prostatectomy procedure. The difficulty lies in placing a needle and suture at the correct angle and with the correct amount of tissue thickness to accomplish a secure and accurate connection. This is especially true in the case of the laparascopic radical prostatectomy where the entire operation is performed through multiple small puncture sites in the abdominal wall fascia using fiber-optic visualization and a variety of tubular small diameter (<15 mm) working ports. During laparascopic radical prostatectomy, the correct placement of a minimum of four stitches to complete this anastomosis can take more than an hour.

Therefore, a need exists for a system and method for quickly and accurately suturing first and second tissue sections in anastomosis and other procedures.

SUMMARY OF THE INVENTION

The present invention relates to a suturing system and method for suturing first and second tissue sections. The system includes an elongate member having paired first distal and proximal channels for receiving portions of a first suture. The first distal channel extends in the elongate member from the proximal end to a first distal aperture and receives the distal end portion and at least a part of the body portion of the first suture. The first proximal channel extends in the elongate member from the proximal end to a first proximal aperture and receives the proximal end portion and at least a part of the body portion of the first suture. The elongate member is moved between the first and second tissue sections as required to achieve the optimum entry position for each needle. The first proximal aperture is at a distance from the first distal aperture and the device is manipulated so that the distal end of the first suture passes through the first tissue section and the proximal end of the first suture passes through the second tissue section.

The elongate member can include indicia on an outer surface for providing reference markings for positioning the elongate member. The distal end of the elongate member can be provided with a flexible tip to facilitate insertion. The flexible tip can be integral to the elongate member or the distal end of the elongate member can have a threaded stud for attaching the flexible tip. In one embodiment, the first distal channel has a curved section leading to the first distal aperture. The first proximal channel can also have a curved section leading to the first proximal aperture.

The distal and proximal end portions of the first suture each can have a needle attached thereto to facilitate passage through tissue. In this regard, the system can also include a needle pusher for advancing or withdrawing one of the needles through the first distal or proximal channel. The needles are made of a material having elasticity to allow the needles to bend through the curved section of either the first distal or proximal channel and then straighten partially or completely after passing therethrough. A shape memory material, for example, a nickel titanium alloy or the like, is such a material. In one embodiment, each of the needles has a radius and can recover to being substantially straight after having been bent to as small as about eight times the needle radius.

In order to allow suture removal from the channels, the elongate member will be made as a multi-component piece. For example, the elongate member can include a central longitudinal section in which the first distal and proximal channels extend and a first outer longitudinal section mating with the central longitudinal section. Each of the channels has a side open to the exterior of the central longitudinal section and the first outer longitudinal section covers the open side of the first distal and proximal channels.

Other paired channels can be provided in the elongate member to accommodate additional sutures. For example, the elongate member can include a second distal channel extending in the elongate member from the proximal end to a second distal aperture and configured and dimensioned to receive the distal end portion and at least a part of the body portion of the second suture; and a second proximal channel extending in the elongate member from the proximal end to a second proximal aperture and configured and dimensioned to receive the proximal end portion and at least a part of the body portion of the second suture. When the elongate member is positioned through the first and second tissue sections with the second needle and suture in the second distal and second proximal channels such that a part of the body portion extends from the proximal end of the elongate member, the distal end of the second suture may be passed through the first tissue section and then the proximal end of the second suture can be positioned so that the proximal needle passes through the second tissue section. As a result, the second suture passes through both the first and second tissue sections.

In order to cover both the first and second set of paired channels, the elongate member can comprise a central longitudinal section in which the first distal and proximal channels and the second distal and proximal channels extend (each of the channels having a side open to the exterior of the central longitudinal section), a first outer longitudinal section mating with the central longitudinal section to cover the open side of the first distal and proximal channels, and a second outer longitudinal section mating with the central longitudinal section to cover the open side of the second distal and proximal channels.

In one embodiment, the central longitudinal section has first and second alignment bores and each of the first and second outer longitudinal sections has an alignment prong.

The alignment prong of the first outer longitudinal section is insertable in the first alignment bore and the alignment prong of the second outer longitudinal section is insertable in the second alignment bore to mate the central and first and second longitudinal sections. One or more flexible rings can be used to fasten together the central and first and second longitudinal sections.

The present invention allows for the quick and efficient placement of needles and sutures. This is beneficial as it makes it technically easier and reduces errors in placing needles and sutures during surgery and decreases the amount of time required to perform the essential repair of the urethra, in the case of radical prostatectomy, or other difficult suturing operations. The foregoing and other features of the present invention will be apparent from the following more particular description of embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The forgoing and other features and also the advantages of the invention will be apparent from the following detailed description taken in conjunction with the accompanying drawings. Additionally, the left-most digit of a reference number identifies the drawing in which the reference number first appears.

DETAILED DESCRIPTION OF THE INVENTION

In the description which follows, any reference to either direction or orientation is intended primarily and solely for purposes of illustration and is not intended in any way as a limitation to the scope of the present invention. Also, the particular embodiments described herein, although being preferred, are not to be considered as limiting of the present invention.

Figures 1, 2, 3:
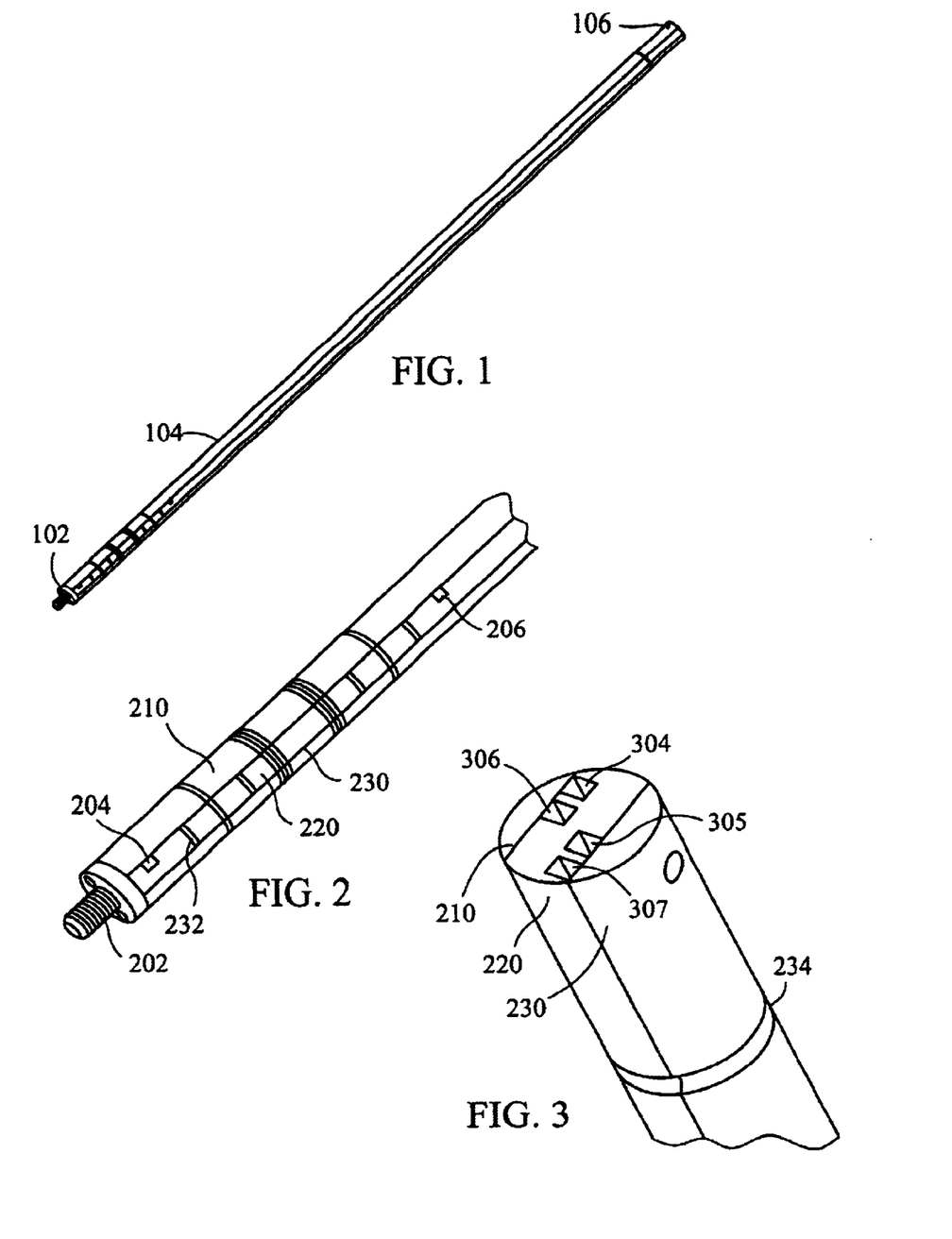
FIG. 1 is a perspective view of one embodiment of an elongate member for a suturing system according to the present invention.
FIG. 2 is a perspective view of the distal portion of the elongate member of FIG. 1.
FIG. 3 is a perspective view of the proximal portion of the elongate member of FIG. 1.

FIG. 1 shows that the suturing system for suturing first and second tissue sections according to the present invention includes an elongate member 104. Elongate member 104 is shown substantially in the shape of a rod, which is particularly useful for guiding elongate member within a lumen of a passage to perform an anastomosis or other procedure. Other shapes can be used to suit a specific application. A proximal end 106 of elongate member 104 is the end nearest to the user and a distal end 102 is the end furthest from the user. Thus, elongate member 104 is inserted, distal end 102 first, into the first and second tissue sections.

In one specific application, discussed in more detail below, elongate member 104 is used for anastomosis during radical prostatectomy. In a radical prostatectomy, elongate member 104 is inserted through the urethra and up into the bladder. In this application, elongate member 104 is of a size and length to be passed through the adult male urethra. That is, elongate member 104 is of a length long enough such that distal end 102 passes into the bladder, while the user is still manually holding proximal end 106, which extends past the end of the penis. As an example, elongate member 104 is a cylinder with an outside diameter of about 8 to 10 mm and a length of about 350 mm.

FIG. 2 shows more detail of distal end 102 of elongate member 104. Distal end 102 has a threaded protrusion 202 onto which may be attached, or screwed, a tip (not shown). Such a tip would facilitate entry of elongate member 104 into the first and second tissue sections. In one alternative, the tip would comprise a simple rounded metal tip and could be integral to elongate member 104. In the case where elongate member 104 is being used for anastomosis during radical prostatectomy, the tip would comprise a softer, flexible "catheter tip" leader. The tip is intended to make repeated passage of the rod through the urethra safer and easier. The tip can be disposable or reusable.

FIG. 2 shows that elongate member 104 comprises three longitudinal members—a first outer longitudinal section 210, a central longitudinal section 220 and a second outer longitudinal section 230. Member 210 comprises the upper part of elongate member 104 in FIG. 2, member 220 comprises the center part of elongate member 104 in FIG. 2 and member 230 comprises the lower part of elongate member 104 in FIG. 2. Elongate member 104 is divided longitudinally into three members 210, 220 and 230 that can be quickly and accurately assembled and disassembled by simple mechanical means. One possible embodiment of the assembly and disassembly process are described in greater detail below.

FIG. 2 further shows a set of indicia 232 along the outer surface of elongate member 104. These indicia, shown in the form of ridges/circumferential markings, are located at predefined distances from each other. This provides information to the user regarding the placement of elongate member 104. Specifically, the user can view the ridges/circumferential markings to accurately position elongate member 104 and, consequently, the needle and sutures. Elongate member 104 also is provided with grooves 234 (FIG. 3) used for placing one or more rings, such as rubber rings or O-ring, along elongate member 104 to secure members 210, 220 and 230 together when elongate member 104 is assembled. During disassembly of elongate member 104, the ring(s) are removed and members 210, 220 and 230 can be separated.

Figures 5A, 5B:
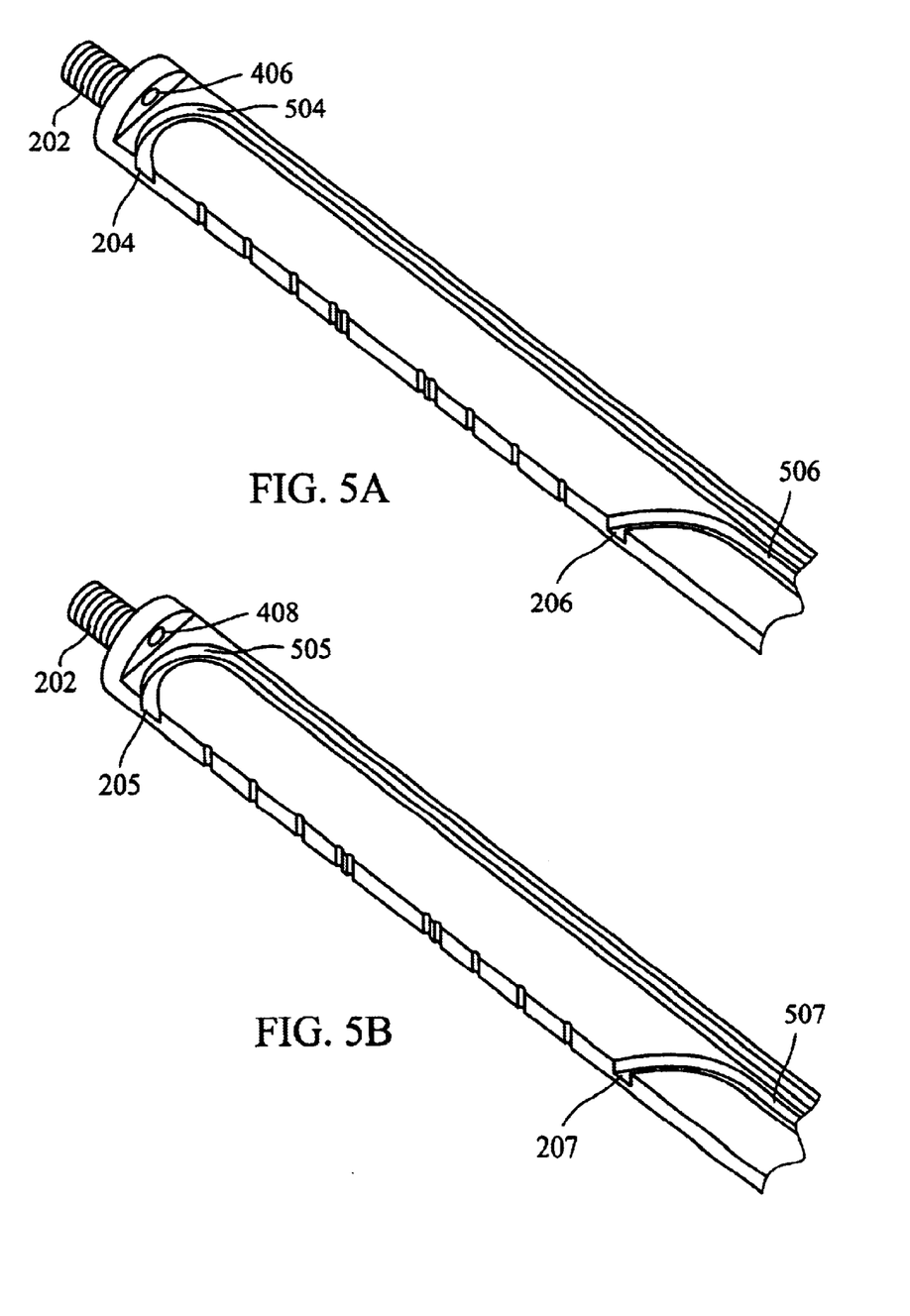
FIG. 5A is a perspective view of a superior side of the distal portion of a central longitudinal member of the elongate member.
FIG. 5B is a perspective view of an inferior side of the distal portion of a central longitudinal member of the elongate member.
Figure 7:
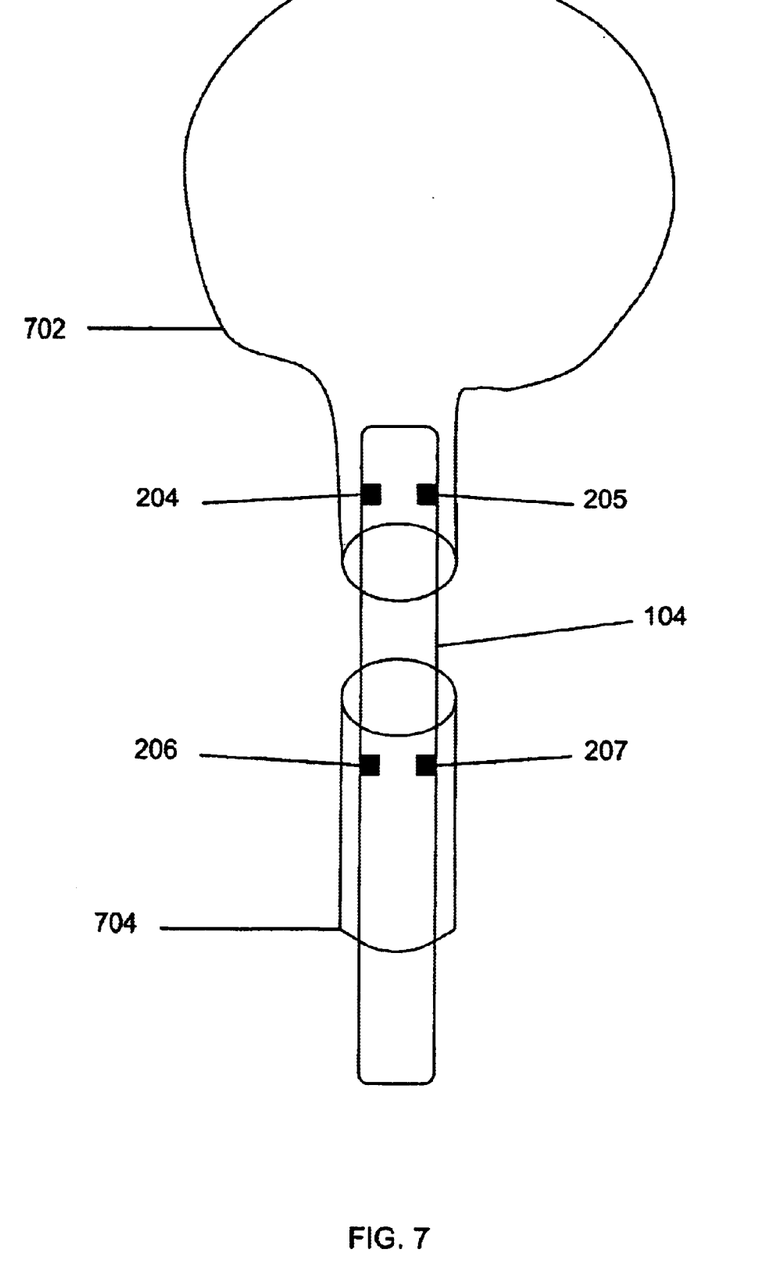
FIG. 7 is a schematic representation showing the use of the elongate member of FIG. 1 for anastomosis during radical prostatectomy.

FIG. 2 also shows exit orifices—a first distal aperture 204 and a first proximal aperture 206. These first distal and proximal exit apertures 204 and 206 are utilized for the exit of a needle and suture from elongate member 104 during use. The first distal and proximal exit apertures 204 and 206 are the ends of channels that are formed in one or more of the members 210, 220 and 230. The channels are described in greater detail below. Shown in FIGS. 5B and 7 are second distal exit aperture 205 and second proximal exit aperture 207, which are located opposite to first distal and proximal exit apertures 204 and 206, respectively, on the other side of elongate member 104. The arrangement of first and second exit orifices 204, 205, 206 and 207 is further described below.

FIG. 3 is a drawing of elongate member 104, showing more detail of proximal end 106. FIG. 3 shows entrance orifices 304, 305, 306 and 307. These entrance orifices 304, 305, 306 and 307 are utilized for the entrance of a needle and suture into elongate member 104. The entrance orifices 304, 305, 306 and 307 are the ends of channels that are formed in one or more of the members 210, 220 and 230. It should be noted that each entrance orifice is connected to an exit orifice via a channel. Specifically, first distal channel entrance orifice 304 corresponds to first distal aperture 204, second distal channel entrance orifice 305 corresponds to second distal aperture 205, first proximal channel entrance orifice 306 corresponds to first proximal aperture 206 and second proximal channel entrance orifice 307 corresponds to second proximal aperture 207.

Figure 4:
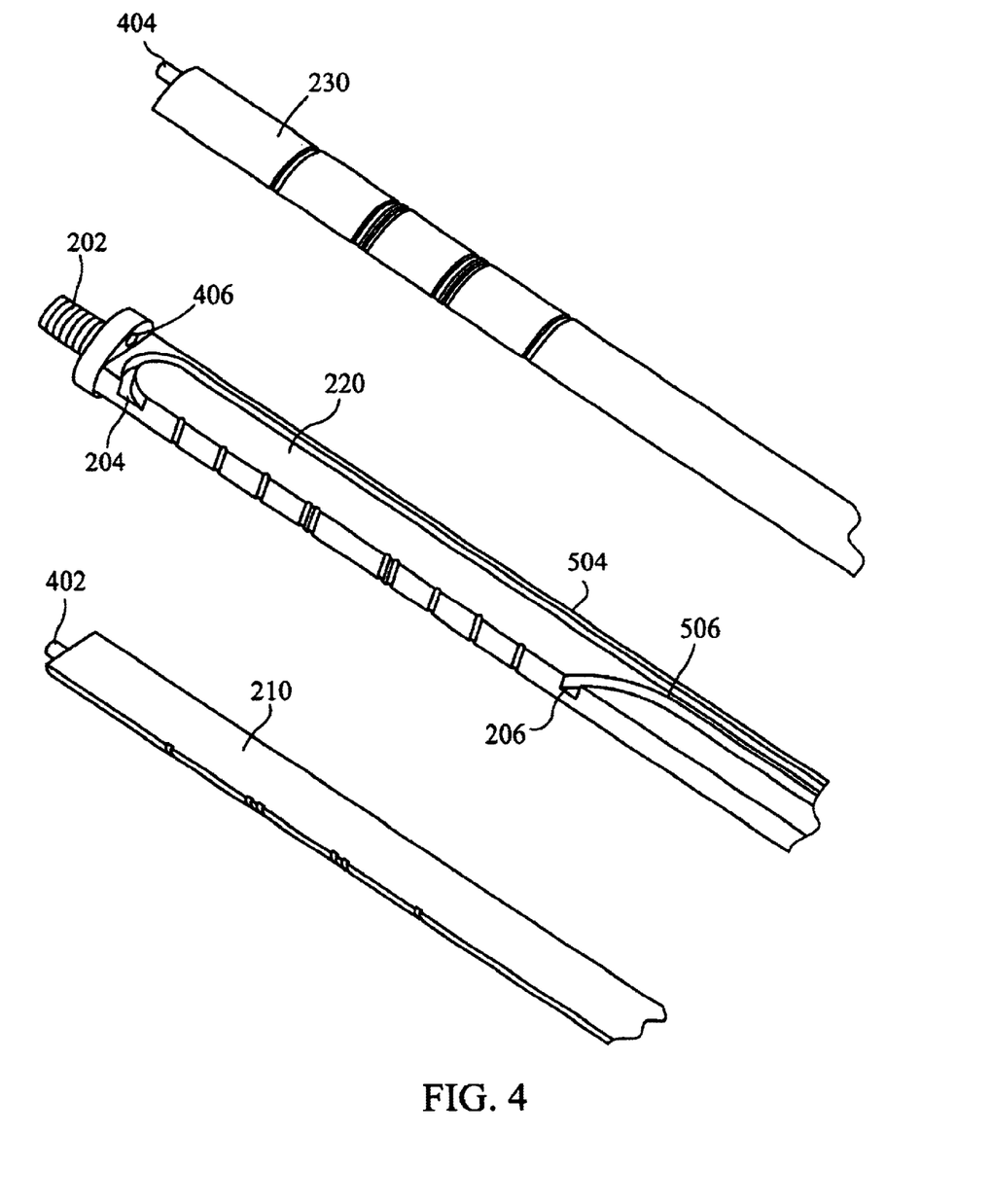
FIG. 4 is a perspective view of the distal portion of the elongate member of FIG. 1 in a disassembled condition.

FIG. 4 is a drawing of elongate member 104, showing more detail of distal end 102 in a disassembled state. A peg 402 is provided on the distal end of first outer longitudinal section 210 and a peg 404 is provided on the distal end of second outer longitudinal section 230. An opening 406 is located on a collar on the distal end of central longitudinal section 220. Upon assembly of elongate member 104, peg 404 is inserted in opening 406, which fastens member 230 to the central member 220. An opening 408 (FIG. 5B), which is located opposite to opening 406, is provided on the opposite end of the collar on the distal end of central longitudinal section 220. Upon assembly of elongate member 104, peg 402 is inserted into opening 408, which fastens member 210 to central member 220.

Figure 6:
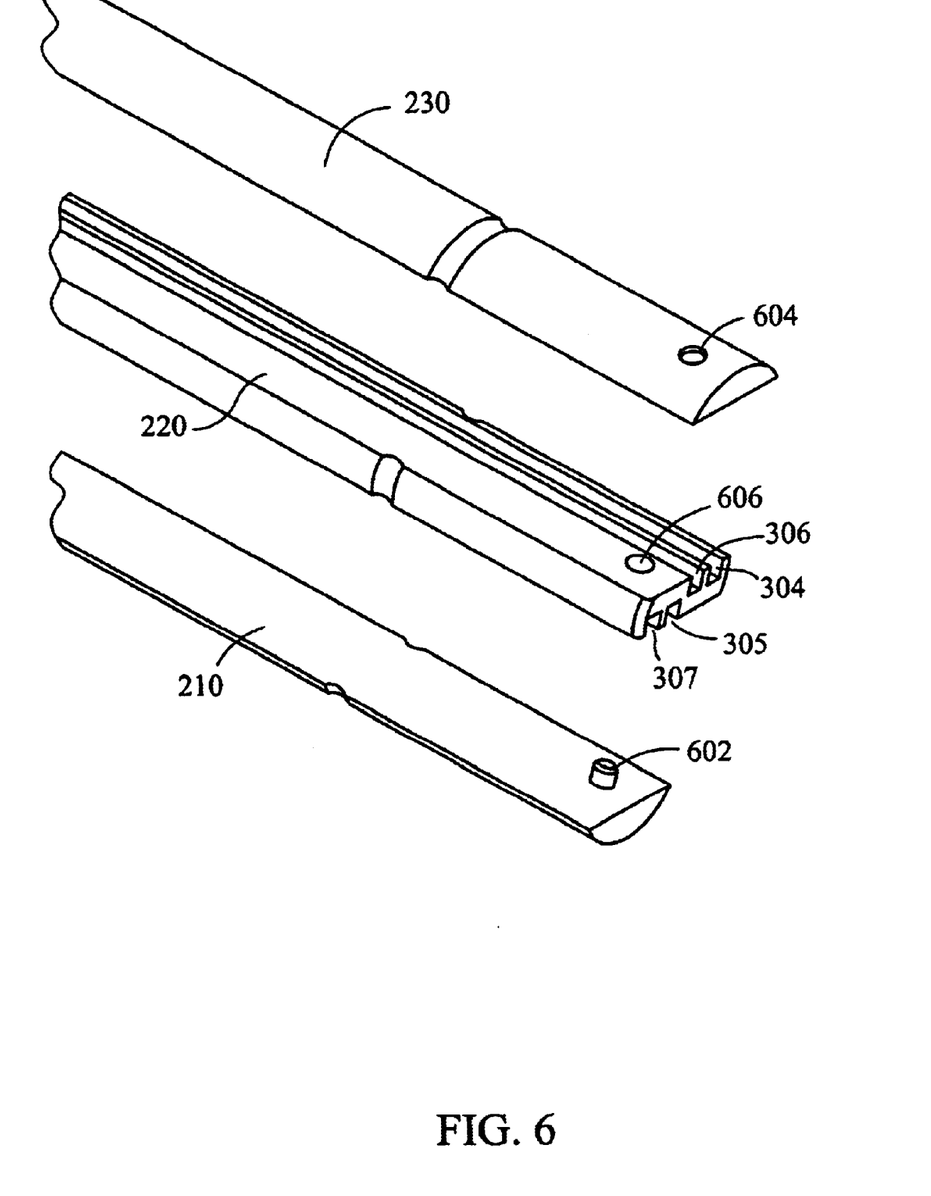
FIG. 6 is a perspective view of the proximal portion of the elongate member of FIG. 1 in a disassembled condition.

A first distal channel 504 terminates with first distal aperture 204 and a first proximal channel 506 terminates with first proximal aperture 206. As best seen in FIG. 6, first distal channel 504 originates at first distal channel entrance orifice 304 and first proximal channel 506 originates at first proximal channel entrance orifice 306. First distal and proximal channels 504 and 506 are located in central longitudinal section 220 so that when elongate member 104 is assembled, first outer longitudinal section 210 covers channels 504 and 506. Thus, sutures are held within these channels as elongate member 104 is manipulated. When elongate member 104 is disassembled, first distal and proximal channels have an open side throughout their entire length. Thus, sutures that are in these channels can be readily accessed.

First distal and proximal channels 504 and 506 are paired with each other so that, as described in more detail below, one section of a suture can travel through first distal channel 504 and the other section of the same suture can travel through first proximal channel 506. Elongate member 104 can be provided with any number of paired channels to suit particular application.

In this regard, FIG. 5B shows elongate member 104 is provided with a second set of paired channels. A second distal channel 505 terminates with second distal aperture 205 and a second proximal channel 507 terminates with second proximal aperture 207. As best seen in FIG. 6, second distal channel 505 originates at second distal channel entrance orifice 305 and second proximal channel 507 originates at second proximal channel entrance orifice 306. Second distal and proximal channels 505 and 507 are located in central longitudinal section 220 so that when elongate member 104 is assembled, second outer longitudinal section 230 covers channels 505 and 507. Thus, sutures are held within these channels as elongate member 104 is manipulated. When elongate member 104 is disassembled, second distal and proximal channels have an open side throughout their entire length. Thus, sutures that are in these channels can be readily accessed.

Channels 505 and 507 are shown located opposite to channels 504 and 506, i.e., on the opposite side of member 220. However, the spatial relationship of channels 504, 505, 506 and 507 can be changed to suit a particular application. Further, in the shown embodiment of the present invention, channels 504, 505, 506 and 507 are substantially straight as they progress from proximal end 102 of elongate member 104 and are each provided with a curved section leading to their terminations, i.e. exit orifices 204, 205, 206 and 207, respectively. The exit angles for exit orifices 204, 205, 206 and 207 from elongate member 104 are chosen for the particular application. As shown, the exit angles are fixed. However, as set forth below in more detail, the present invention also envisions adjustable exit angles. For example, in one embodiment the distal portion of the channels can be made of a flexible material and a control wire (or other mechanism) coupled to the flexible portion and leading to the proximal end of the elongate member can then be manipulated to adjust the exit angle of the exit orifice.

FIG. 6 shows that, analogous to distal end 102, proximal end 106 of elongate member 104 includes an alignment and coupling mechanism. A peg 602 is located on the proximal end of member 230 and a peg 604 is located on the proximal end of member 210. An opening 606 is located on the proximal end of central member 220, and a second opening (not shown) is located on the proximal end of member 210. Upon assembly of elongate member 104, peg 602 is inserted in opening 606 and peg 604 is inserted into the second opening.

The use and operation of the suturing system according to the present invention will now be described with reference to FIGS. 7-10 and using anastomosis during radical prostatectomy as a non-limiting example. As previously explained, radical prostatectomy involves the removal of the prostate gland along with its fascial coverings and requires amputating the junctions of the prostate to the urethra at the urogenital diaphragm and to the urinary bladder at the bladder neck. This results in the disconnection of the urethra from the bladder. Anastomosis using the apparatus of the present invention seeks to reconnect the urethra with the bladder.

FIG. 7 shows that elongate member 104 is inserted into the penis, through urethra 704 and further into bladder 702. Elongate member 104 is sized and positioned so that exit orifices 204 and 205 are lined up with the bladder 702 such that the exit of a suture from exit orifices 204 and 205 will intersect with the membrane of bladder 702. FIG. 7 further shows that exit orifices 206 and 207 are lined up with urethra 704 such that the exit of a suture from exit orifices 206 and 207 will intersect with the membrane of urethra 704.

Figure 8:
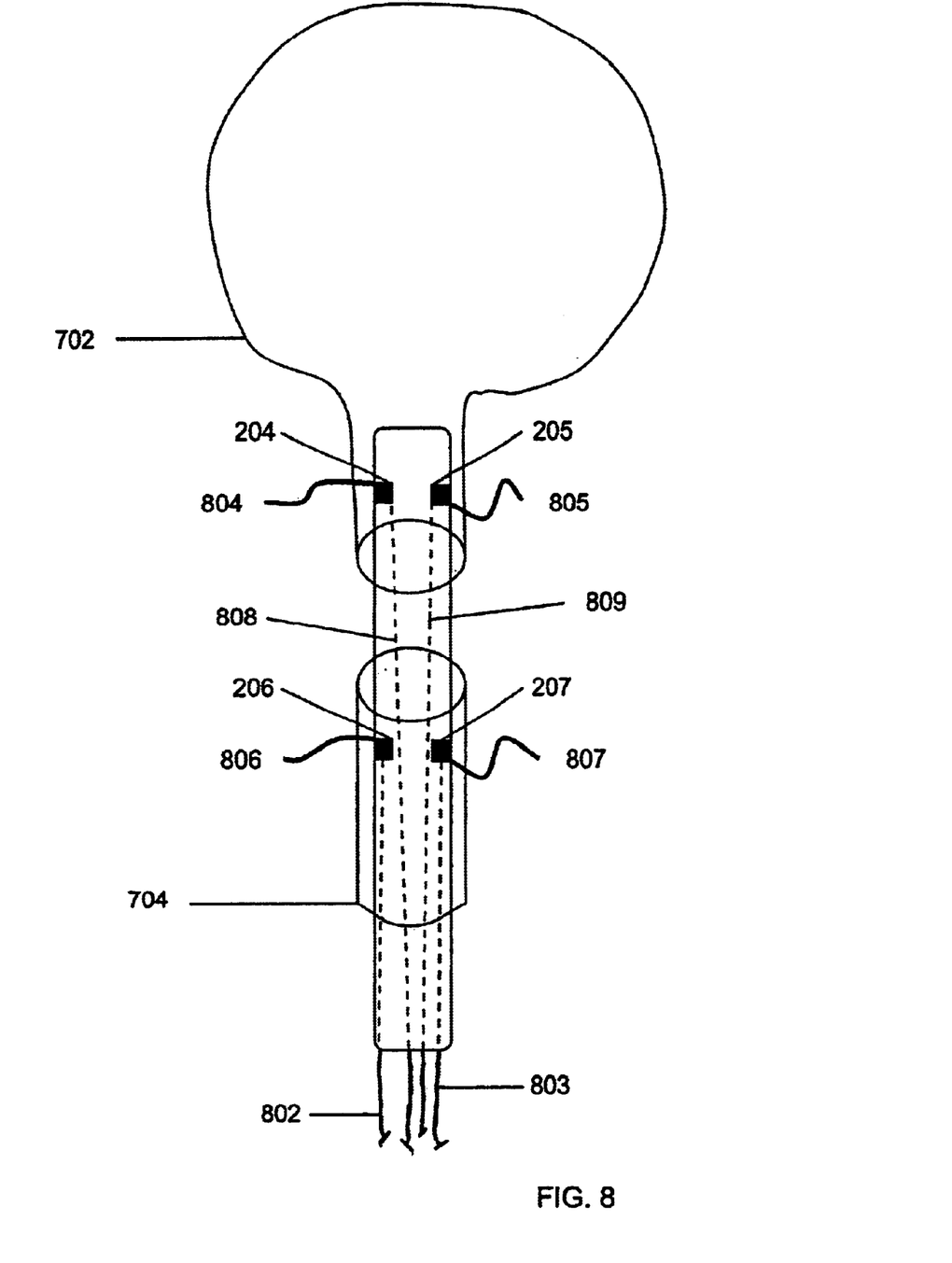
FIG. 8 is a schematic representation showing the elongate member of FIG. 7 with a suture.

As shown in FIG. 8, a first suture 802 is provided with a distal end portion 804, a proximal end portion 806 and a body portion 808 located therebetween. Similarly, a second suture 803 is provided with a distal end portion 805, a proximal end portion 807 and a body portion 809 located therebetween. As used throughout this specification, the term "suture" refers to any elongated, generally filamentous element for connecting first and second tissue sections. This term refers to both biodegradable and non-degradable materials and can be a single strand or multiple stands. Additionally, a needle or other structure for facilitating insertion of first and second sutures 802 and 803 through tissue can be provided on any of end portions 804, 805, 806 and 807. The desirability of such a structure depends on a number of factors including the mechanical properties of the tissue, the mechanical properties of the sutures, user preference, etc.

The suture insertion process begins with the insertion of distal end portion 804 of first suture 802 into first distal channel entrance orifice 304. Proximal end portion 806 of first suture 802 is inserted into first proximal channel entrance orifice 306. Distal end portion 804 and at least a part of body portion 808 of first suture 802 are pushed through first distal channel 504. Proximal end portion 806 and another part of body portion 808 of first suture 802 are pushed through first proximal channel 506. First suture 802 has a length so that a loop of body portion 808 extends from first distal and proximal apertures 204 and 206. The loop can be pulled if placement of first suture 802 needs to be readjusted. Second suture 803 is placed in second distal and proximal channels 505 and 507 in an analogous fashion.

When first suture 802 is sufficiently moved through first distal and proximal channel 504 and 506, distal end portion 804 exits through first distal aperture 204 and proximal end portion 806 exits through first proximal aperture 206. Similarly, when second suture 803 is sufficiently moved through second distal and proximal channel 505 and 507, distal end portion 805 exits through second distal aperture 504 and proximal end portion 807 exits through second proximal aperture 207. Thus, distal end portion 804 of first suture 802 and distal end portion 805 of second suture 803 pierce bladder 702. Likewise, proximal end portion 806 of first suture 802 and proximal end portion 807 of second suture 803 pierce urethra 704.

In one embodiment, the piercing of the membrane of bladder 702 and the membrane of urethra 704 is performed using fiber-optic visualization through an abdominal port in a laparoscopic procedure. For example, as each suture is pushed out of its respective exit orifice and is forced through its respective member, laparascopic forceps clutch the suture and pull it through its respective membrane. Further, laparascopic forceps clutch the suture and pull it out of the respective membrane. In another embodiment, the piercing of the membrane of bladder 702 and the membrane of urethra 704 is performed using direct visualization in an open procedure. Regardless of whether an open or laparoscopic procedure is used, elongate member 104 can be longitudinally and/or rotationally moved so that first distal and proximal apertures 204 and 206 and second distal and proximal apertures 205 and 207 are in the desired rotation and longitudinal position in bladder 702 or urethra 704.

Although elongate member 104 is set up so that pairs of sutures may be placed as polar opposites (i.e. first distal aperture 204 is located approximately 180° from second distal aperture 205 and first proximal aperture 206 is located approximately 180° from second proximal aperture 207), using alternative techniques with this invention will allow sutures to be placed circumferentially around the gaping ends of the neck of bladder 702 and urethra 704 in any sequence and as many as desired. The exit angles for the sutures from the elongate member are chosen so that they provide the most useful entry and exit angles for a suture either coming from within the urethra or from within the bladder. The separation between each set of exit ports is fixed at a distance that gives the operator adequate mobility to place the bladder neck stitch and then the urethral stitch in their ideal locations simultaneously rather than in sequence, if desired. Direct observation of the circumferential centimeter markings on the elongate member between these exit ports easily seen in the gap between the bladder neck and urethra enables accurate positioning. Alternative embodiments allow for alternative locations of exit ports and indicia.

Once the end portions of first and second sutures 802 and 803 have pierced bladder 702 and urethra 704, first and second sutures 802 and 803 are extricated from elongate member 104. Since each of channels 504, 505, 506 and 507 has an open side that is exposed when elongate member 104 is disassembled by uncoupling first and second outer longitudinal sections 210 and 230 from central longitudinal section 220, first and second sutures 802 and 803 can be removed from elongate member 104. Elongate member 104 can be disassembled while still in position. Alternatively, elongate member 104 can be disassembled after it is removed from urethra 704. In this alternative, the loop of suture material that extends out of proximal end 106 of elongate member 104 should be of sufficient length (at least as long as elongate member 104).

It should be noted that the present invention envisions mechanisms other than the use of a multi-piece elongate member 104 to remove the sutures from the elongate member. For example, elongate member 104 can be made as a single piece that has channels with an open side covered by a cover that slides open. The slidable cover keeps the sutures in the channels and can be moved so that the sutures can be removed from the channels. Alternatively, the open side can have a resilient flap that can be bent to allow removal of the sutures. Other embodiments are described below with reference to FIGS. 12–16.

Figure 9:
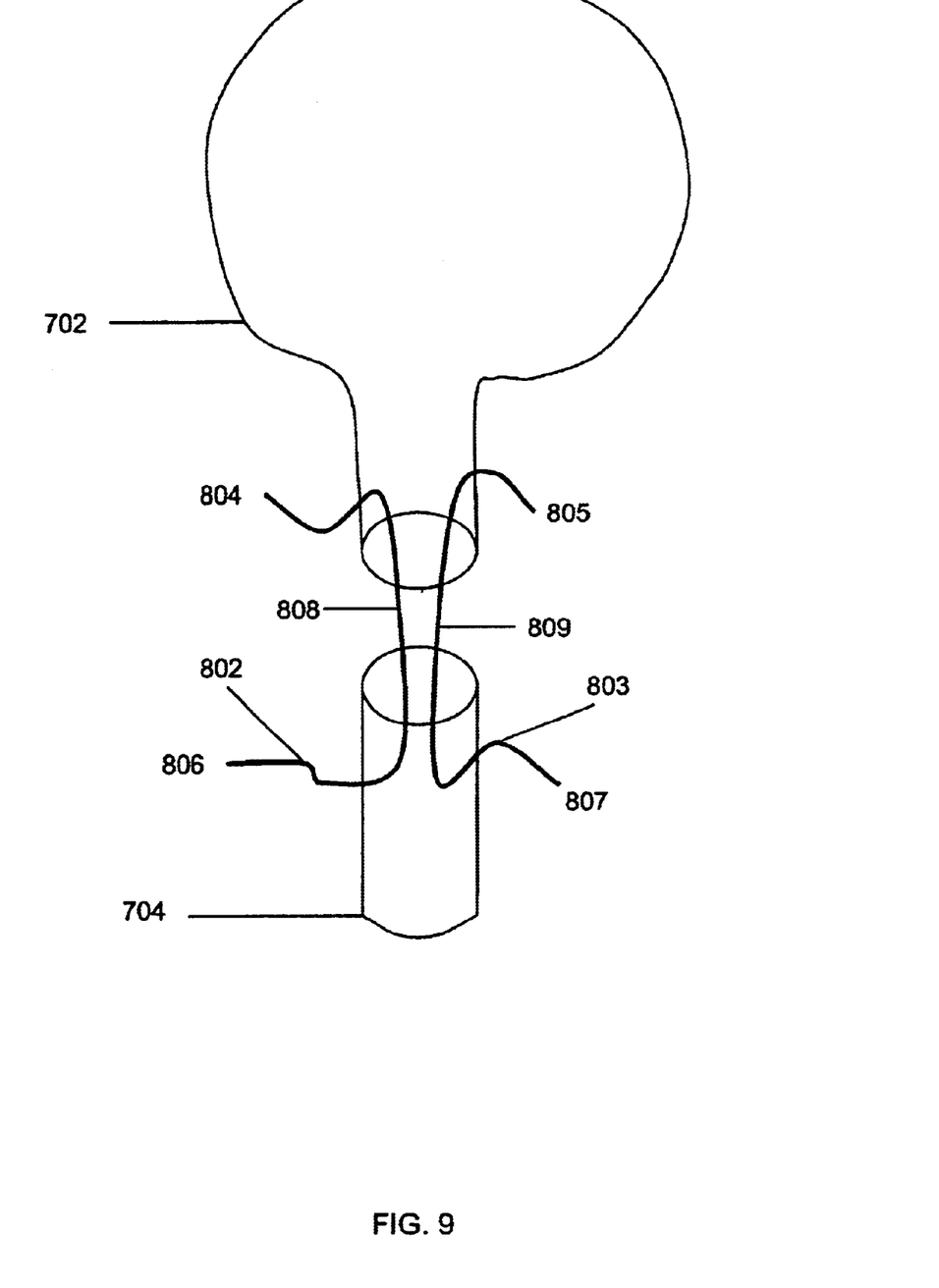
FIG. 9 is a schematic representation showing two sutures inserted in the bladder and urethra.

FIG. 9 shows first and second sutures 802 and 803 freed from elongate member 104. Although FIG. 9 shows elongate member 104 completely removed from the patient, all or part of elongate member 104 may still be in the patient while the sutures are tightened to draw bladder 702 and urethra 704 together. If desired, elongate member 104 can be loaded with additional sutures and the process of inserting these sutures in bladder 702 and urethra 704 can be repeated. In some cases, four sutures will be sufficient for a urethrovesical anastomosis, so that only two passes of elongate member 104 will be needed.

Figure 10:
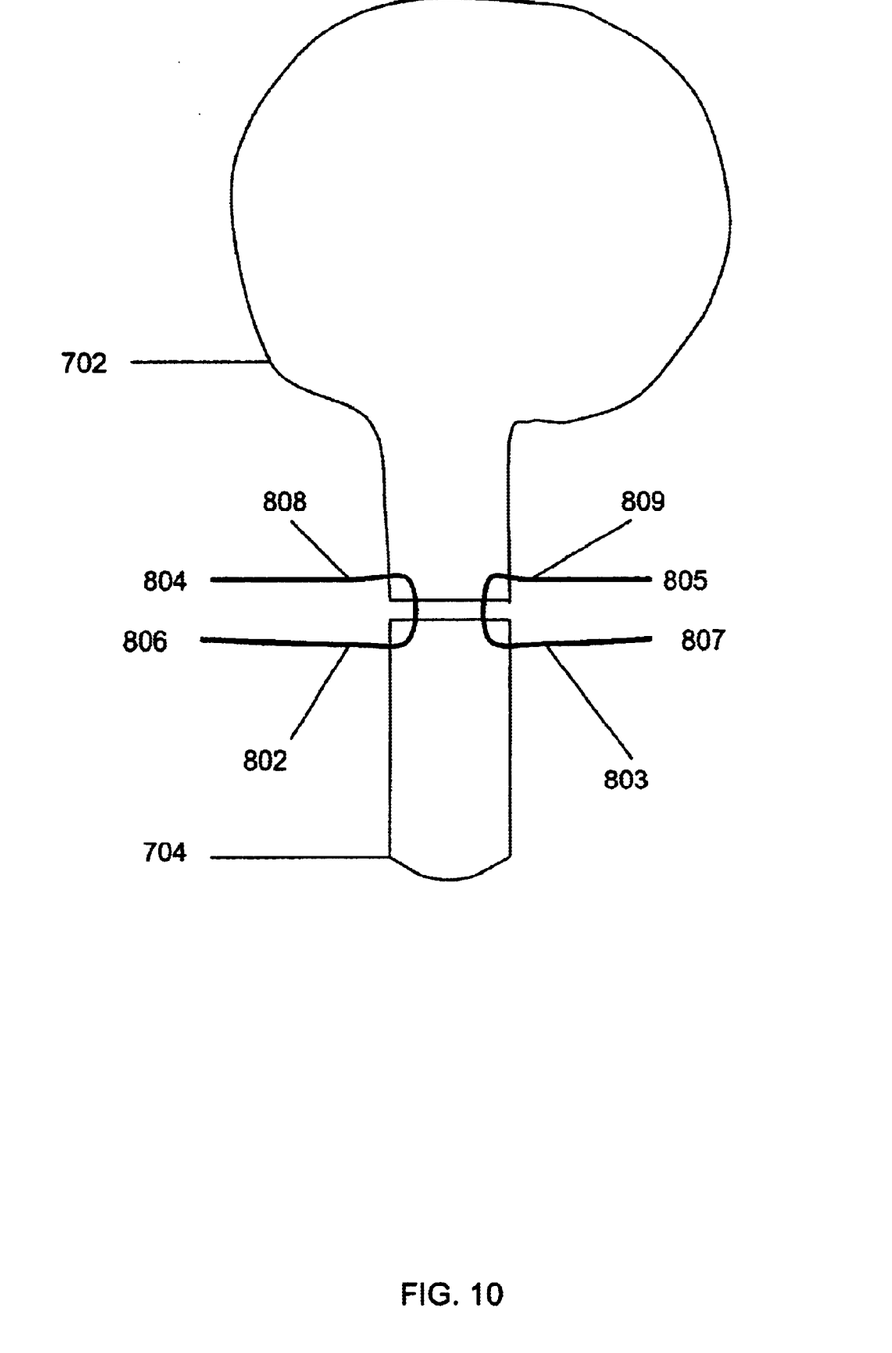
FIG. 10 is a schematic representation showing the sutures of FIG. 9 drawing the bladder and urethra together.

FIG. 10 depicts the suture tightening process, which can occur after all sutures have been inserted through bladder 702 and urethra 704, or, alternatively after each pass of elongate member 104. Specifically, distal and proximal end portions 804 and 806 of first suture 802 are pulled and distal and proximal end portions 805 and 807 of second suture 803 are pulled. This pulling process draws bladder 702 and urethra 704 closer together, and ultimately places bladder 702 in contact with urethra 704. When the desired apposition of bladder 702 and urethra 704 is achieved, the sutures can be tied with knots or otherwise secured together (e.g. with a suture anchor). This secures bladder 702 with urethra 704 and promotes the healing of the two tissue sections together.

Figure 11:
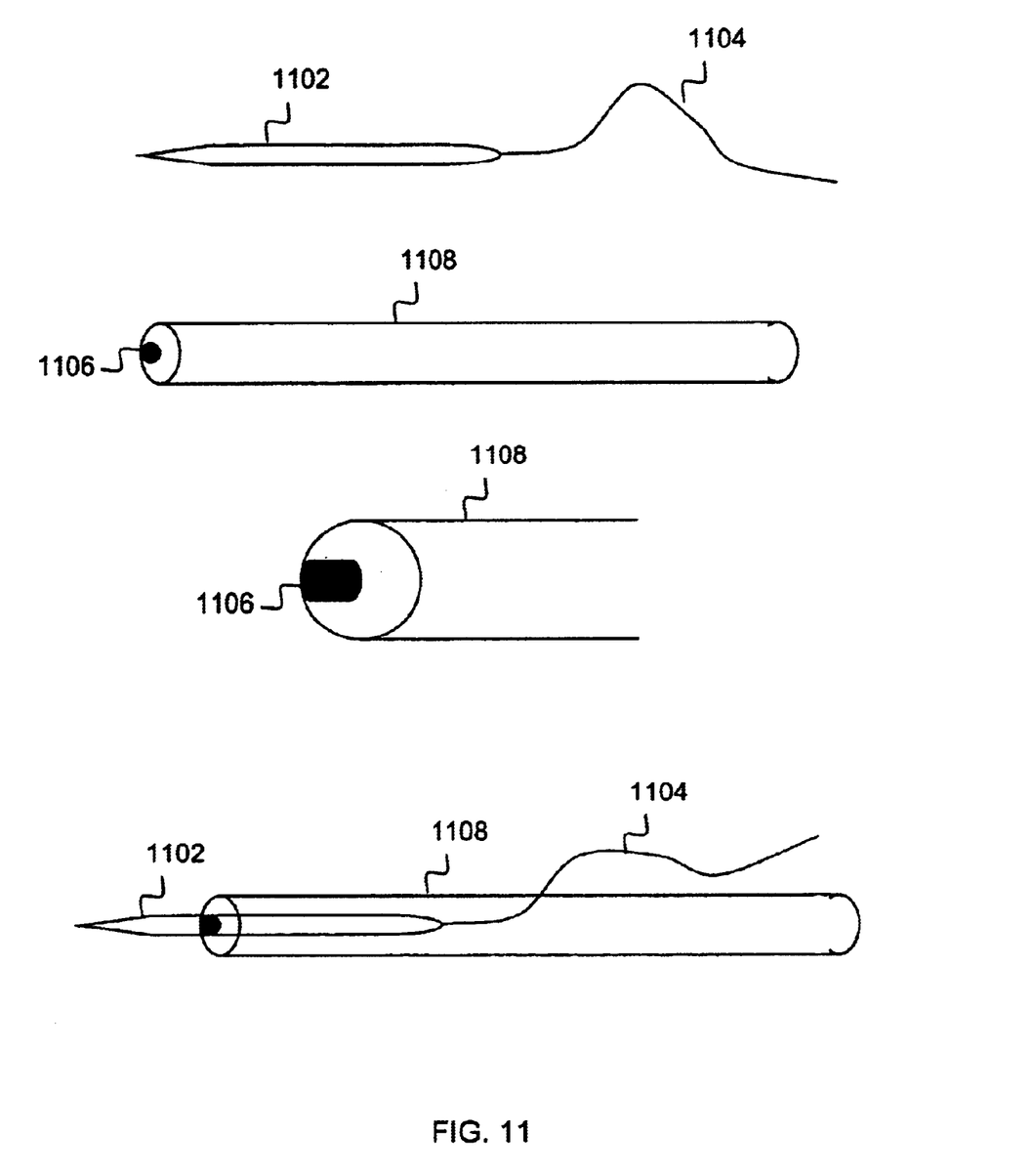
FIG. 11 is a perspective view of a needle, suture, and pushing member according to the present invention.

As previously noted, the sutures can be provided with a needle and a pushing device can be used to facilitate moving the sutures in their respective channels. FIG. 11 shows an embodiment of a needle, suture and pushing member of the present invention. A needle 1102 is constructed of a super-elastic material, such as nickel titanium alloy or other material with similar characteristics (e.g. thin spring steel), to achieve the desired singular deflection at the exit orifice from the rod 104 before returning to a "normally straight" shape after exiting. The use of a material (plastic or metal alloy) to construct needle 1102 such that it exhibits shape-memory is preferable so that the needles have elasticity to allow the needles to bend through the curved section of the channel and then straighten after passing therethrough. In this embodiment, needle 1102 will be substantially straight at rest and have sufficient shape-memory recovery characteristics such that it can be bent to a radius of eight times its own radius and return to its initial straight shape, or substantially so, when released. A nickel titanium alloy (50:50 NITINOL) is an example of such a super-elastic material that could be used to make needle 1102. In addition, thin steel alloy ("spring steel") needles could be used to make needle 1102 in some embodiments where a lesser degree of bending can be used.

In an embodiment of the present invention, suture 1104 will either be permanently attached to needle 1102 at manufacture, if needle 1102 is to be single-use, or will have mechanical means of attachment to needle 1102, if the needles are reusable. In the previous example, suture 1104 should be of sufficient length to extend through the entire urethra 704, up through any abdominal laparoscopy ports with both ends and still have a sufficient length of continuous loop to allow for withdrawal of elongate member 104 from urethra 704 before disassembly of elongate member 104.

In an embodiment of the present invention, needle 1102 is approximately 1.2 mm in maximum diameter and 4 cm in length. A sharp point will be created on one end of needle 1102. At the other end of needle 1102 is formed a round hole (about 0.6 mm) made at right angles to the centerline axis of needle 1102, near the blunt end (within 5 mm) of needle 1102. A longitudinal channel of about 0.4 mm width and 0.6 mm depth is formed from the blunt end of needle 1102 to the hole. A long (1 meter) suture 1104 of about 2-0 size (about 4 mm diameter) will have a common ball swaged to each end, which manually press fits into the hole in the blunt end of the needle 1102, allowing the trailing suture 1104 to fit into the channel. Alternatively, if a monofilament material were used for suture 1104, a custom shape could be formed on the end of the material and fit into a matching slot and receiving shape in needle 1102. Alternatively, the needles could be disposable and the suture material can be swaged onto the blunt end.

FIG. 11 further shows a pushing member 1108, constructed of flexible plastic or metal. The pushing member 1108 has a slit 1106 formed into the tip of one end. This slit is formed such that it fits a portion of the blunt end of needle 1102 (including an attached suture 1104) and allows the trailing suture 1104 to run along side. This permits pushing member 1108 to come up flush against needle 1102 to facilitate placement into and through channels 504, 505, 506 and 507 in elongate member 104.

At the bottom of FIG. 11 is shown an example of needle 1102 (with attached suture 1104) inserted into slit 1106 formed in pushing member 1108. Suture 1104 runs along side pushing member 1108. In this form, pushing member 1108 pushes needle 1102 (with attached suture 1104) through the respective channel in elongate member 104 until it exits from an exit orifice, as described in the suture insertion process of FIG. 8.

Figure 12:
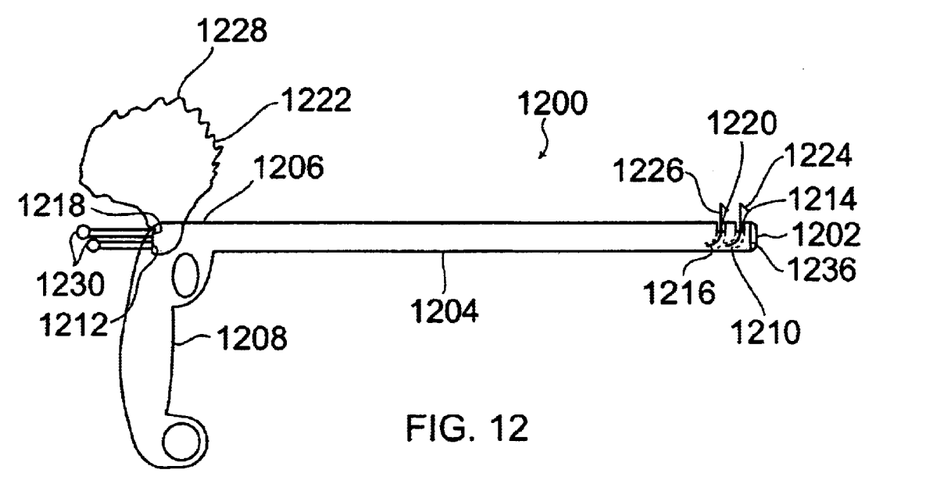
FIG. 12 is a side view of another embodiment of a suturing system according to the present invention.
Figure 13:
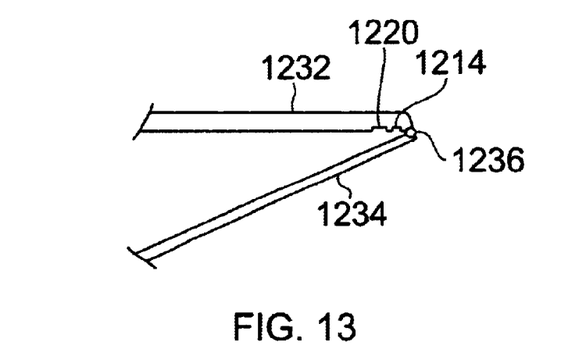
FIG. 13 is a top view of the distal portion of the suturing system of FIG. 12.

FIGS. 12 and 13 show another embodiment of a suturing system 1200 according to the present invention. An elongate member 1204 has a distal end 1202 and a proximal end 1206. Proximal end 1206 includes a handle 1208 to facilitate use and manipulation. A first distal channel 1210, only a portion of which is shown in cross section, runs from a first distal entrance orifice 1212 to a first distal exit aperture 1214. A first proximal channel 1216, only a portion of which is shown in cross section, runs from a first proximal entrance orifice 1218 to a first proximal exit aperture 1220.

In use, a first suture 1222 can be inserted in first distal and proximal channels 1210 and 1216. A distal end portion 1224 of first suture 1222 runs through first distal channel 1210 and a proximal end portion 1226 of first suture 1222 runs through first proximal channel 1216 such that a body portion 1228 of first suture 1222 extends from first distal and proximal entrance orifices 1212 and 1218. Pusher members 1230 can be used to move the suture through the channels.

As best seen in FIG. 13, elongate member 1204 is made in two components, a left section 1232 and a right section 1234. A hinge member 1236 allows left and right sections 1232 and 1234 to pivot with respect to one another so that first distal and proximal channels 1210 and 1216 can be accessed. This allows the suture to be removed from the channels so that after the ends of the suture (and if appropriate any needles that are attached to these ends) have been passed through tissue, the ends of the suture can be pulled to draw the tissue together.

Figure 14:
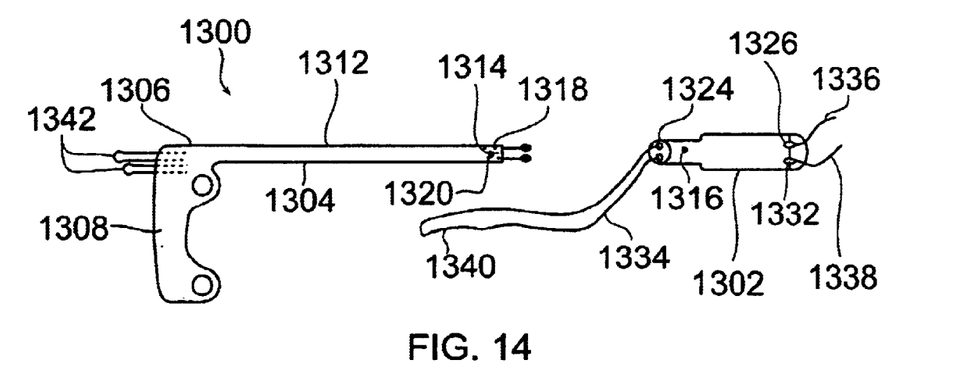
FIG. 14 is a side view of another embodiment of a suturing system according to the present invention with the distal portion of the elongate member separated.
Figure 15:
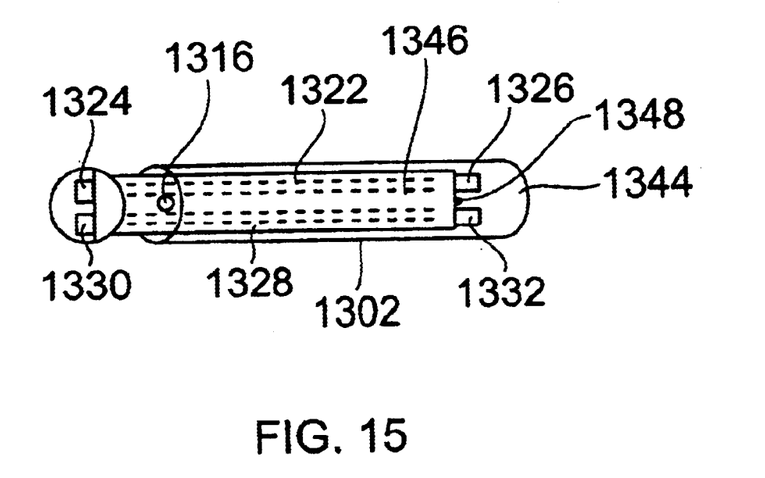
FIG. 15 is a top view of the distal portion of FIG. 14.
Figure 16:
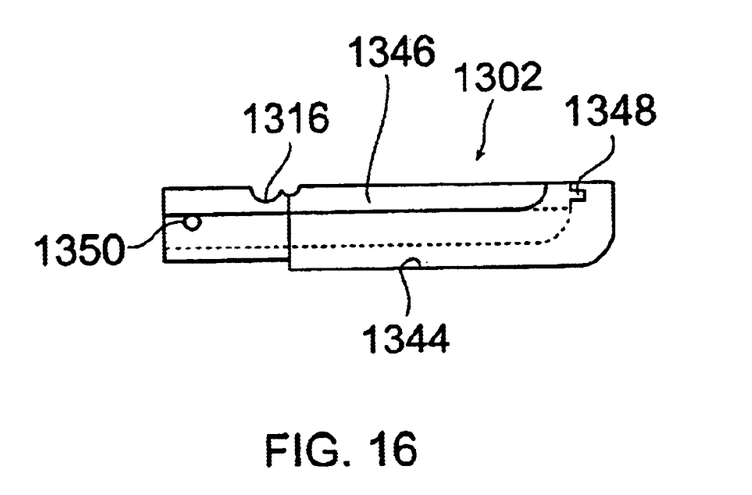
FIG. 16 is a side view of the distal portion of FIG. 14.

FIGS. 14–16 show another embodiment of a suturing system 1300 according to the present invention. A distal end member 1302 is removably attachable to an elongate member 1304. A proximal end 1306 of elongate member 1304 includes a handle 1308 to facilitate use and manipulation. A body 1312 of elongate member 1304 has a ball detent 1314 and distal end member 1302 has a recess 1316 that couples with ball detent 1314 in order to removably attach distal end member 1302 to elongate member 1304. Other mechanisms could be used.

A first distal body channel 1318, only a portion of which is shown in cross section, runs through body 1312 of elongate member 1304. A first proximal body channel 1320, only a portion of which is shown in cross section, runs through body 1312 of elongate member 1304. End member 1302 has analogous channels. Specifically, a first distal end member channel 1322 runs from a first distal entrance orifice 1324 to a first distal exit aperture 1326. A first proximal end member channel 1328 runs from a first proximal entrance orifice 1330 to a first proximal exit aperture 1332. When end member 1302 is coupled to body 1312, first distal body channel 1318 aligns with first distal end member channel 1322 to form the first distal channel, and first proximal body channel 1320 aligns with first proximal end member channel 1328 to form the first proximal channel.

Because distal end member 1302 removably attaches to body 1312 of elongate member 1304, end members having different exit angles of exit orifices 1326 and 1332 can be constructed and the end member having the desired exit angles can be selected for a particular application. It should be noted that for a given end member, first distal exit orifice 1326 need not have the same exit angle as first proximal exit orifice 1332.

In use, a first suture 1334 can be inserted in first distal and proximal channels 1322 and 1328 of end member 1302. A distal end portion 1336 of first suture 1334 runs through first distal channel 1322 and a proximal end portion 1338 of first suture 1334 runs through first proximal channel 1328 such that a body portion 1340 of first suture 1334 extends from first distal and proximal entrance orifices 1324 and 1330. Pusher members 1342 can be used to move the suture through the channels. In this embodiment, first suture 1334 need not run through the channels (first distal and proximal body channels 1318 and 1320) of body 1312 of elongate member 1304. As a result, elongate member 1304 need not be made in separable components. If elongate member 1304 is not made in separable components, body portion 1340 of first suture 1334 can run along the outside of elongate member 1304. Alternatively, body portion 1340 of first suture 1334 can be fitted into the interior of either body 1312 of elongate member 1304 or distal end member 1302.

As best seen in FIGS. 15 and 16, distal end member 1302 is made in two components, a housing 1344 and a cover 1346. Housing 1344 contains first distal and proximal channels 1322 and 1328 and cover 1346 can be removed to expose these channels and thereby extricate the suture from the channels after it has passed through tissue. Housing 1344 and/or cover 1346 can be provided with a coupling mechanism that readily allows for attachment and detachment. Examples of such mechanisms include a locator and lock 1348 and a locating pin 1350.

While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A suturing system for suturing first and second tissue sections comprising:
    a first suture having distal and proximal end portions and a body portion therebetween;
    an elongate member with proximal and distal ends;
    a first distal channel extending in the elongate member from the proximal end to a first distal aperture and configured and dimensioned to receive the distal end portion and at least a part of the body portion of the first suture;
    a first proximal channel extending in the elongate member from the proximal end to a first proximal aperture and configured and dimensioned to receive the proximal end portion and at least a part of the body portion of the first suture,
    wherein the distal end portion of the first suture is disposed within the first distal channel, the proximal end portion of the first suture is disposed within the first proximal channel, and a part of the body portion of the first suture extends from the proximal end of the elongate member.

2. The suturing system of claim 1 wherein the first proximal aperture is located a spaced longitudinal distance from the first distal aperture.

3. The suturing system of claim 2 wherein the first distal aperture of the first distal channel is adjacent a first tissue section and the first proximal aperture of the first proximal channel is adjacent a second tissue section such that the distal end of the first suture passes through the first tissue section and the proximal end of the first suture passes through the second tissue section so that the first suture passes through both the first and second tissue sections.

4. The suturing system of claim 1 wherein the elongate member includes indicia on an outer surface for providing reference markings for positioning the elongate member.

5. The suturing system of claim 1 wherein the distal end of the elongate member includes a flexible tip.

6. The suturing system of claim 5 wherein the distal end of the elongate member includes a threaded stud for attaching the flexible tip.

7. The suturing system of claim 1 wherein each of the distal and proximal end portions of the first suture has a needle attached thereto.

8. The suturing system of claim 7 wherein the first distal channel has a curved section leading to the first distal aperture.

9. The suturing system of claim 8 wherein the first proximal channel has a curved section leading to the first proximal aperture.

10. The suturing system of claim 9 wherein the needles are made of a material having elasticity to allow the needles to bend through the curved section of either the first distal or proximal channel and then straighten after passing therethrough.

11. The suturing system of claim 10 wherein the needles are made of a shape memory material.

12. The suturing system of claim 11 wherein the needles are made of a nickel titanium alloy.

13. The suturing system of claim 11 wherein each of the needles has a radius and can be bent to a bent radius about eight times the needle radius.

14. The suturing system of claim 7 further comprising a needle pusher for moving one of the needles through the first distal or proximal channel.

15. The suturing system of claim 1 wherein the elongate member comprises:
    a central longitudinal section in which the first distal and proximal channels extend, each of the channels having a side open to the exterior of the central longitudinal section; and
    a first outer longitudinal section mating with the central longitudinal section to cover the open side of the first distal and proximal channels.

16. The suturing system of claim 15 wherein the central longitudinal section and the first outer longitudinal section are pivotably coupled.

17. A suturing system for suturing first and second tissue sections comprising:
    a first suture having distal and proximal end portions and a body portion therebetween;
    an elongate member with proximal and distal ends;
    a first distal channel extending in the elongate from the proximal end to a first distal aperture and configured and dimensioned to receive the distal end portion and at least a part of the body portion of the first suture;
    a first proximal channel extending in the elongate member from the proximal end to a first proximal aperture and configured and dimensioned to receive the proximal end portion and at least a part of the body portion of the first suture;

a second suture having distal and proximal end portions and a body portion therebetween;

a second distal channel extending in the elongate member from the proximal end to a second distal aperture and configured and dimensioned to receive the distal end portion and at least a part of the body portion of the second suture; and a second proximal channel extending in the elongate member from the proximal end to a second proximal aperture and configured and dimensioned to receive the proximal end portion and at least a part of the body portion of the second suture, wherein the distal end portion of the first suture is disposed within the first distal channel, the proximal end portion of the first suture is disposed within the first proximal channel, and a part of the body portion of the first suture extends from the proximal end of the elongate member, wherein the distal end portion of the second suture is disposed within the second distal channel, the proximal end portion of the second suture is disposed within the second proximal channel, and a part of the body portion of the second suture extends from the proximal end of the elongate member.

18. The suturing system of claim 17 wherein the elongate member comprises:

a central longitudinal section in which the first distal and proximal channels and the second distal and proximal channels extend, each of the channels having a side open to the exterior of the central longitudinal section;

a first outer longitudinal section mating with the central longitudinal section to cover the open side of the first distal and proximal channels; and a second outer longitudinal section mating with the central longitudinal section to cover the open side of the second distal and proximal channels.

19. The suturing system of claim 18 wherein the central longitudinal section has first and second alignment bores and each of the first and second outer longitudinal sections has an alignment prong, the alignment prong of the first outer longitudinal section insertable in the first alignment bore and the alignment prong of the second outer longitudinal section insertable in the second alignment bore to mate the central and first and second longitudinal sections.

20. The suturing system of claim 19 further comprising at least one flexible ring for fastening together the central and first and second longitudinal sections.

* * * * *

UNITED STATES PATENT AND TRADEMARK OFFICE
CERTIFICATE OF CORRECTION

PATENT NO. : 6,821,283 B2
DATED : November 23, 2004
INVENTOR(S) : Winston E. Barzell et al.

It is certified that error appears in the above-identified patent and that said Letters Patent is hereby corrected as shown below:

Column 12,
Line 58, replace "a first distal channel extending in the elongate from the" with
-- a first distal channel extending in the elongate member from the --.

Signed and Sealed this

Twenty-ninth Day of November, 2005

JON W. DUDAS
*Director of the United States Patent and Trademark Office*